(12) United States Patent
Kim et al.

(10) Patent No.: US 8,559,900 B2
(45) Date of Patent: *Oct. 15, 2013

(54) METHOD AND SYSTEM FOR DATA COMMUNICATION USING A BODY

(75) Inventors: Tae-Song Kim, Seoul (KR); Jong-Oh Park, Seoul (KR); Byung-Kyu Kim, Seoul (KR); Jin-Seok Kim, Seoul (KR); Han Cheung, Daejeon (KR); Won-Woo Cho, Daejeon (KR); Nan-Young Yoon, Daejeon (KR); Young-Rok Kim, Daejeon (KR)

(73) Assignee: Korea Institute of Science and Technology, Seoul (KR)

( * ) Notice: Subject to any disclaimer, the term of this patent is extended or adjusted under 35 U.S.C. 154(b) by 122 days.

This patent is subject to a terminal disclaimer.

(21) Appl. No.: 13/195,294

(22) Filed: Aug. 1, 2011

(65) Prior Publication Data

US 2011/0286722 A1    Nov. 24, 2011

Related U.S. Application Data

(62) Division of application No. 12/210,073, filed on Sep. 12, 2008, now Pat. No. 8,155,586.

(30) Foreign Application Priority Data

Jan. 25, 2003  (KR) .................. 10-2003-0005059

(51) Int. Cl.
    *G06F 3/033* (2013.01)

(52) U.S. Cl.
    USPC .......... 455/130; 455/41.1; 455/128; 128/899; 128/903; 600/160

(58) Field of Classification Search
    USPC ................. 455/41.1, 128, 130; 128/899, 903; 600/160
    See application file for complete search history.

(56) References Cited

U.S. PATENT DOCUMENTS

| 6,239,788 B1 * | 5/2001 | Nohno et al. | 345/173 |
| 6,314,315 B1 * | 11/2001 | Hung et al. | 600/547 |
| 6,804,558 B2 * | 10/2004 | Haller et al. | 607/30 |

* cited by examiner

*Primary Examiner* — Tuan H Nguyen
(74) *Attorney, Agent, or Firm* — NSIP Law

(57) ABSTRACT

A portable device for data communication using a body as a conductor to transmit data to a receiver, the portable device includes a data receiving unit to receive data, a controller unit to control processing of data to be transmitted, a current limiting circuit to limit a current of a signal corresponding to the data to be transmitted to a predetermined value, and transmitting electrodes connected to the current limiting circuit and to contact the body to transmit the signal having the current of predetermined value to the receiver.

7 Claims, 11 Drawing Sheets

METHOD AND SYSTEM FOR DATA COMMUNICATION USING A BODY

CROSS-REFERENCE TO RELATED APPLICATION

This application is a divisional of U.S. patent application Ser. No. 12/210,073 filed on Sep. 12, 2008, now U.S. Pat. No. 8,155,586, which claims the benefit under 35 U.S.C. §120 of a U.S. patent application Ser. No. 10/543,143 filed on Jul. 22, 2005, which claims the benefit under 35 U.S.C. §119(a) of a Korean Patent Application No. 10-2003-0005059, filed on Jan. 25, 2003 in the Korean Intellectual Property Office. The entire disclosures of the related applications are hereby incorporated by reference.

TECHNICAL FIELD

The following description relates to a method and system for data communication with respect to a body, and to transmitting data from a sensor placed in the human body to the outside of the human body to collect information, wherein a current generated from the sensor flows through the human body acting as a conductor to transmit the data.

BACKGROUND

Various sensors for collecting information, for example, medical information in the human body have been developed and used. In addition to a technique for collecting information in the human body, a technique for transmitting the collected information to the outside of the human body is important.

A communication cable method is one of general data transmitting methods. A communication cable method is applied to, for example, an endoscope which is developed for observing the stomach and the intestines. In the communication cable method, a cable made of a conducting wire or an optic fiber is inserted into the human body through a throat of a patient. While the communication cable method has high reliability and high data quality, it may cause severe pain to the patient.

In order to solve the above-mentioned problem, Given Imaging LTD. in Israel has developed a capsule type endoscope called M2A. When a patient swallows the capsule type endoscope in a form of a tablet, video data in the human body photographed by a camera of the endoscope are transmitted to an external-receiving unit, and displayed in a monitor.

However, in the capsule type endoscope, since a radio wave is used to transmit a signal, power consumption is large, an operation time is short, and the receiving sensitivity is deteriorated due to interference of various electric waves from the outside of the human body. In addition, radio-transmitting apparatus such as a converter circuit for converting a video signal into a high frequency signal and an antenna for signal transmission, etc. may be required. Accordingly, the volume and production cost may be increased. Also, the high frequency may be harmful to the human body.

SUMMARY

Accordingly, according to an aspect, there is provided a method and system for data communication with respect to the human in which a current generated flows through the human body to transmit data to the outside of the human body.

According to another aspect, there is provided a portable device for data communication using a body as a conductor to transmit data to a receiver, the portable device comprising a data receiving unit to receive data, a controller unit to control processing of data to be transmitted, a current limiting circuit to limit a current of a signal corresponding to the data to be transmitted to a predetermined value, and transmitting electrodes connected to the current limiting circuit and to contact the body to transmit the signal having the current of predetermined value to the receiver.

The signal may be transmitted by controlling a voltage polarity of the transmitting electrodes.

The data receiving unit may comprise a lighting device and a lens, and the portable device may be a capsule type endoscope further comprising a pixel array to capture image data through the lens, a read circuit to fetch signals of the pixel array, a coding circuit to code an output signal of the read circuit, a switching circuit connected to the current limiting circuit to transmit a signal coded in the coding circuit through the transmitting electrodes, an oscillating circuit to determine an operational frequency, and a power source.

The portable device may further comprise a data storage to store the data received, an interfacing unit to interface with a user, and a modulator for modulating a signal corresponding to the data stored in the data storage, decoded by the controller unit, wherein the current limiting circuit limits a current of the modulated signal to the predetermined value.

The data stored in the data storage may be video and/or audio data, and the portable device may be one of a sound player, an MP3 player, a cellular phone, a portable media player, and a navigation device.

The portable device may further comprise a display unit to display content corresponding to the data stored in the data storage, a sound output unit to convert the signal decoded by the controller unit to an analog signal, and a power source, wherein the data receiving unit comprises a universal serial bus controller and a universal serial bus connector to receive the data.

Each of the transmitting electrodes may be disposed on a rear surface of the portable device in the form of a clip, an 'L' shaped electrode, or a curved surfaced electrode.

The portable device may further comprise a data storage to store the data received, wherein the data stored in the data storage corresponds to an electronic key, and the transmitting electrodes transmits a signal corresponding to the electronic key having a current of the predetermined value to gain access controlled by the receiver.

The portable device may further comprise an encryption unit to encrypt the electronic key, an encoding unit to encode the encrypted electronic key, and a switching circuit to modulate the encoded electronic key to output to the current limiting circuit.

The body may be a human body.

According to still another aspect, there is provided a portable device for data communication using a body as a conductor to transmit data to a receiver, the portable device comprising a controller unit to control processing of data to be transmitted, a current limiting circuit to limit a current of a signal corresponding to the data to be transmitted to a predetermined value, and transmitting electrodes connected to the current limiting circuit and contacted with the body to generate electric potential difference therebetween, so that the signal having the current of predetermined value flows from the transmitting electrode having higher electric potential through the body to the receiver and sinks to the transmitting electrode having lower electric potential.

The number of the transmitting electrodes may be at least two.

The portable device may further comprise a data storage to store the data, and an interfacing unit to interface with a user.

According to still another aspect, there is provided a receiver for receiving data communicated using a body as a conductor to transmit the date, the receiver comprising receiving electrodes to contact the body to receive a signal corresponding to the data, and a signal processor to process the signal received through the receiving electrodes, wherein the signal has a current defined to a predetermined value.

The receiver may be a peripheral device to output a reproduction signal corresponding to video and/or audio data, the processed signal may correspond to an output obtained from reproducing the video and/or audio data, and the peripheral device may further comprise an output unit to output the signal from the signal processor.

The peripheral device may be one of a headset, an earset, an earphone, a visual visor, and a combination thereof.

The output unit may comprises at least one of a sound outputting unit to output sound corresponding to the signal, and a display unit to output an image corresponding to the signal.

The signal processor may comprise an amplifier to amplify the signal received through the receiving electrodes, a bandwidth pass filter to extract a baseband signal from the amplified signal, a comparator to convert the baseband signal to a signal of a predetermined voltage, and a controller unit to divide the converted signal and output the divided signals to the output unit.

The data may correspond to an electronic key, and the receiver may further comprise a controller to control access based on the signal received through the receiving electrodes. The signal processor comprises an amplifier to amplify the signal received through the receiving electrodes, a bandwidth pass filter to convert the amplified signal to a baseband signal, a comparator to convert the baseband signal to a signal of a predetermined voltage, a decoding unit to decode the signal of a predetermined voltage, and a decrypting unit to decrypt the decoded signal to output to the controller.

According to still another aspect, there is provided a method of communicating data wirelessly using a body as a conductor to transmit the data from a portable device to a receiver, the method comprising generating a signal corresponding to data to be transmitted, limiting a current of the signal corresponding to the data to be transmitted to a predetermined value, and transmitting the signal having the current of predetermined value to the receiver through transmitting electrodes of the portable device, where the transmitting electrodes contact the body and the body contacts receiving electrodes of the receiver.

The transmitting of the signal may comprise controlling a voltage polarity of the transmitting electrodes to transmit the signal.

The data to be transmitted may be one of video and/or audio data and an electronic key, and the portable device may be one of a sound player, an MP3 player, a cellular phone, a portable media player, a navigation device, and an access requesting device.

According to still another aspect, there is provided a method of communicating data wirelessly using a body as a conductor to transmit the data from a portable device to a receiver, the method comprising controlling transmitting electrodes of the portable device to generate electric potential difference between the transmitting electrodes according to the data to be transmitted, wherein the transmitting electrodes contact the body and the body contacts receiving electrodes of the receiver, limiting a current of the transmitting electrodes to a predetermined value, and supplying the current from the transmitting electrode having higher electric potential to the body so that the current flows in form of digital through the surface of the body to the receiving electrodes of the receiver and sinks to the transmitting electrode having lower electric potential.

The controlling of the transmitting electrodes may allow a voltage polarity of the transmitting electrodes to be changed according to the data to be transmitted.

Other features will become apparent to those skilled in the art from the following detailed description, which, taken in conjunction with the attached drawings, discloses exemplary embodiments of the invention.

BRIEF DESCRIPTION OF THE DRAWINGS

Throughout the drawings and the detailed description, the same drawing reference numerals will be understood to refer to the same elements, features, and structures.

DETAILED DESCRIPTION

The following detailed description is provided to assist the reader in gaining a comprehensive understanding of the methods, apparatuses and/or systems described herein. Accordingly, various changes, modifications, and equivalents of the systems, apparatuses and/or methods described herein will be suggested to those of ordinary skill in the art. Also, descriptions of well-known functions and constructions are omitted to increase clarity and conciseness.

Figure 1:
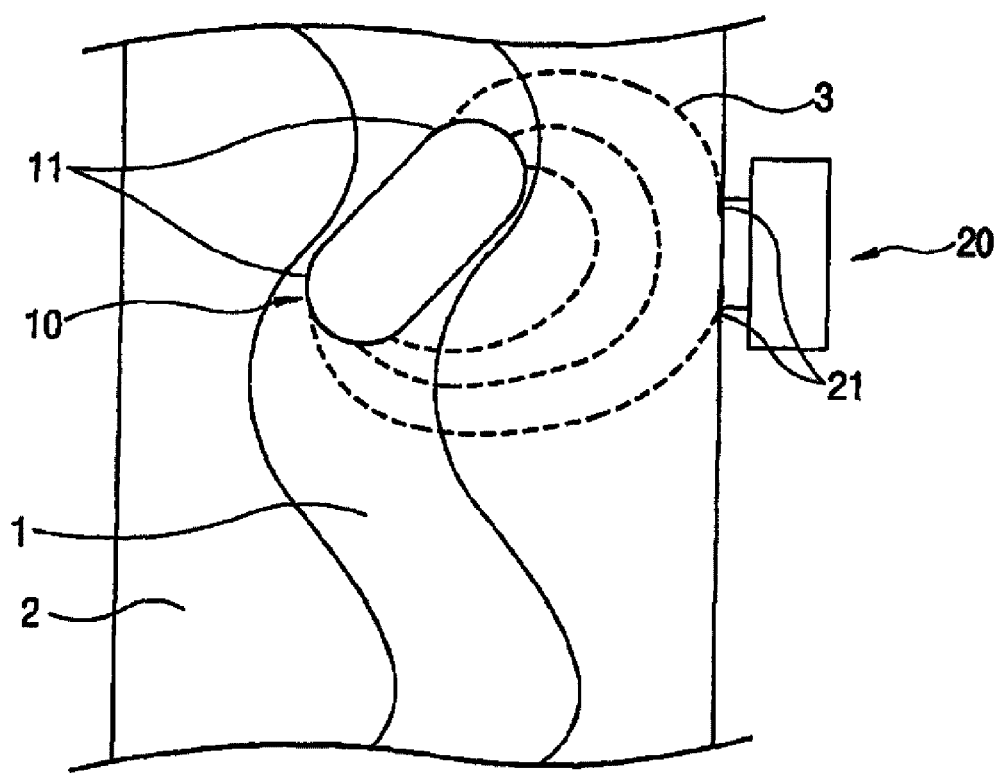
FIG. 1 is a diagram illustrating a method for data communication with respect to the human body in accordance with an exemplary embodiment.

FIG. 1 illustrates a method and a system for data communication with respect to the human body in accordance with an exemplary embodiment. As depicted in FIG. 1, a sensor 10 placed inside the human body 1, for example, in the digestive organs, transmits information of the inside of the human body 1 to a receiver 20 installed on a surface of the human body through the human body 2.

With reference to FIG. 1, a method for data communication in the human body capable of transmitting a signal from the sensor 10 inside the human body 1 to the receiver 20 placed in the outside of the human body will be described. Various information (for example, pictures of the inside of the body, PH, temperature or electric impedance, etc.) collected by the sensor 10 is converted into an electric signal by a signal processing circuit (not shown) of the sensor 10 and is applied to transmitting electrodes 11 through an output line of the signal processing circuit, and accordingly, electric potential difference occurs between the transmitting electrodes 11. Because the transmitting electrodes 11 are contacted to the inside of the human body 1 (it is electrically connected with the human body through, for example, body fluids in the digestive organs), by electric potential difference between the two transmitting electrodes 11, a current 3 flows through the human body 2. The current 3 flows from the transmitting electrode having a higher electric potential through the surface of the human body back into the inside of the human body 1 and is sunken to the transmitting electrode having a lower electric potential. Herein, the current flowing through the surface of the human body induces a voltage between two receiving electrodes 21, and accordingly, a signal transmitted from the sensor 10 placed in the human body 1 may be sensed by the receiver 20 outside of the human body. The receiver 20 restores a video signal by processing the received signal, and displays it on a monitor or stores it in a memory.

FIGS. 2a through 2d illustrate several exemplary embodiments of the transmitting electrodes 11 installed on a surface of the sensor 10 of the system for data communication in the human body. For example, on the surface of the sensor 10, two metal plates, namely, two transmitting electrodes are formed, which are respectively connected to outlines of a signal processing circuit (not shown) of the sensor 10.

Where the two transmitting electrodes are electrically isolated and separated from each other sufficiently, the transmitting electrodes may be formed at any position of the surface of the sensor 10. Herein, according to an aspect, the transmitting electrodes may have a sensor-covering shape, namely, a three-dimensionally curved shape in order to be easily contacted with the inside of the human body. It is understood that the sensor 10 may have other shapes in addition to the shape shown in FIGS. 1 and 2a-2d.

Figure 2A:
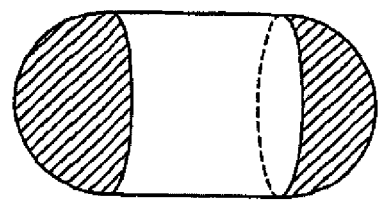
FIGS. 2a through 2d are perspective views illustrating a transmitting electrode installed to a surface of a sensor used in a system for data communication with respect to the human body, in accordance with exemplary embodiments.
Figure 2B:
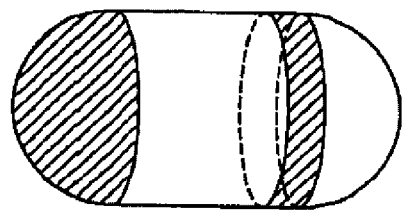
Figure 2C:
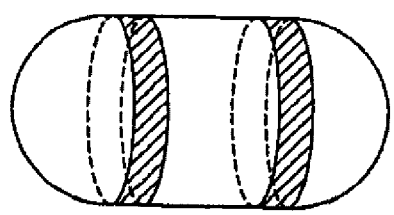
Figure 2D:
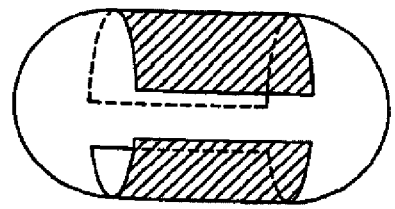

In FIG. 2a, a transmitting electrode comprises a first electrode and a second electrode respectively surrounding the both ends of the sensor. In FIG. 2b, a transmitting electrode comprises a first electrode surrounding an end of the sensor and a second electrode covering the other end of the sensor having a band-shape. In FIG. 2c, a transmitting electrode comprises a first electrode and a second electrode respectively covering both ends of the sensor having a band-shape. In FIG. 2d, a transmitting electrode comprises a first electrode and a second electrode symmetrically formed along a longer axis of the sensor.

Because the transmitting electrodes are exposed to the inside of the human body, it may be made of material having good resistance against corrosion, due to a reactive material such as a digestive fluid, etc., and also harmless to the human body. According to an aspect, SUS316L or gold may be used for the transmitting electrodes. According to an aspect, in order to isolate the transmitting electrodes formed on the surface of the sensor, electrically, the surface of the sensor may be a nonconductor harmless to the human body. For example, peek, polyethylene or polypropylene in a plastic group may be used as a nonconductor harmless to the human body. According to another aspect, parylene may be coated onto the surface of the sensor made of peek, polyethylene or polypropylene.

Figure 3:
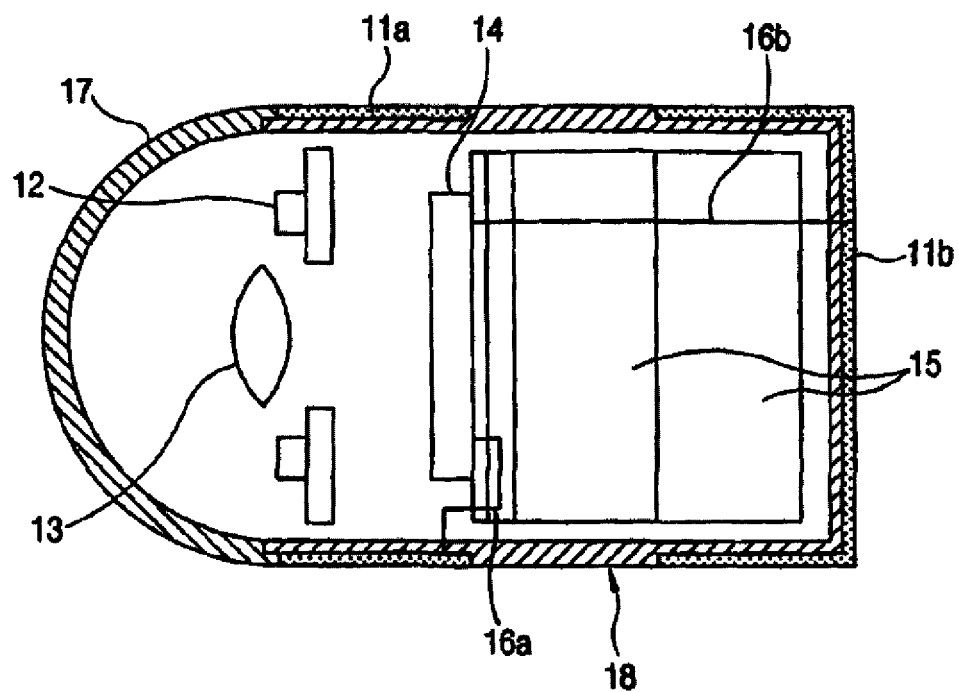
FIG. 3 is a sectional view illustrating a sensor of a system for data communication with respect to the human body in accordance with an exemplary embodiment.

FIG. 3 illustrates an internal structure of a capsule type endoscope used as a sensor in accordance with an exemplary embodiment. Referring to FIG. 3, the capsule type endoscope may have a diameter of 10 mm and a length of 20 mm. A light receiving window 17 having a dome shape is formed in an end of a housing forming an external shape of the capsule type endoscope, and a rectangular container 18 is formed in the other end of the housing. Accordingly, the capsule type endoscope has a bullet shape.

In the capsule type endoscope, the light receiving window 17 which passes light is made of a nonconductor harmless to the human body. The container 18 which contains several devices also is made of a nonconductor harmless to the human body. The light receiving window 17 and the container 18 are sealed so that infiltration of a digestive fluid, etc. into the capsule type endoscope may be prevented and that leakage of substances in the capsule type endoscope into the human body may be avoided.

As depicted in FIG. 3, the capsule type endoscope comprises a lighting device 12, a lens 13, an image sensor 14, such as a CMOS image sensor, a battery 15, and transmitting electrodes 11a and 11b electrically isolated-formed on a surface of the container 18.

The lens 13 is arranged behind the light receiving window 17, and the CMOS image sensor 14 in which various circuits are integrated is arranged behind the lens 13. A distance between the lens 13 and the CMOS image sensor 14 is adjusted so as to focus light incident through the light receiving window 17 on a surface of the CMOS image sensor 14. For example, around the lens 13 and the CMOS image sensor 14, a plurality of lighting devices 12 may be arranged in a donut-shape. According to an aspect, four light emitting diodes (LEDs) may be used for the lighting devices 12. Non-reflection coating may be provided on inner and outer surfaces of the light receiving window 17 so that light irradiated from the lighting devices 12 may pass through the light receiving window 17 and illuminate an object. The battery 15 provided as a power supply may be arranged behind the CMOS image sensor 14. According to an aspect, a silver oxide battery having an even discharge voltage and causing little or no harm to the human body may be used as the battery 15.

An operation of the capsule type endoscope will be described. Where the lighting devices 12 irradiate a light, the CMOS image sensor 14 captures an image of an object through the lens 13. The CMOS image sensor 14 processes the captured video signal through various internal circuits and applies the signal to the transmitting electrodes respectively connected to two output lines 16. Accordingly, receiving electrodes placed outside of the human body may sense the signal, as described above.

Figure 4:
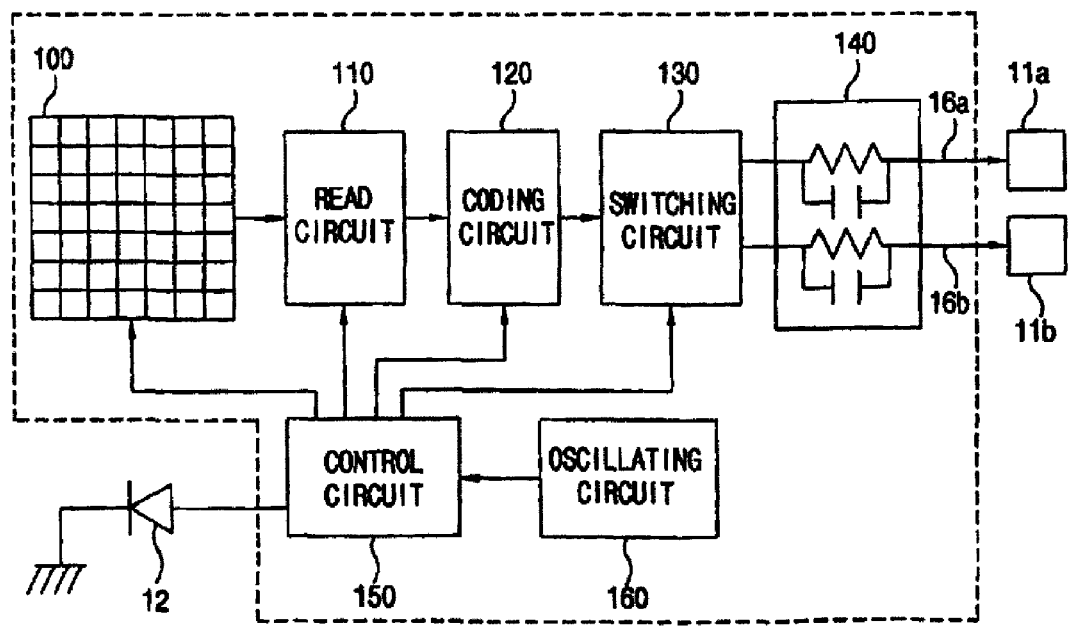
FIG. 4 is a circuit diagram illustrating an internal construction of a CMOS image sensor of a sensor according to an exemplary embodiment.

FIG. 4 illustrates an image sensor, for example, the CMOS image sensor 14 of the capsule type endoscope shown in FIG. 3.

As depicted in FIG. 4, the CMOS image sensor 14 comprises a pixel array 100 for capturing and storing a video signal, a read circuit 110 for fetching a signal of each pixel, for example, sequentially, a coding circuit 120 for coding an output signal of the read circuit 110, a switching circuit 130 for transmitting a signal coded in the coding circuit 120 through the two output lines 16a and 16b, a current limiting circuit 140 for adjusting a current value so as to prevent flowing of a current causing damage to the human body, a control circuit 150 for controlling the signal processing and the operation of the lighting device 12, and an oscillating circuit 160 for determining an operational frequency.

According to an aspect, the pixel array 100 (for example, of 320×240 pixels) may capture and store video signals of high resolution. The read circuit 110 processes the stored video signals sequentially as a frame or more per 1 sec. Accordingly, there may not be a need to have a memory disadvantageous in the cost and volume aspects. According to another aspect, the control circuit 150 determines brightness inside the human body based on brightness of light incident to the pixel array 100 and controls the lighting device 12 to operate variably for, for example, 5~200 msec. The video signals are captured by the pixel array 100 during that time. Accordingly, each video frame may be instantly captured, and the brightness thereof may be improved. A PSK method that is simple and has strong tolerance against noise may be used in encoding.

Where the signal transmitted from the coding circuit 120 is "1", the switching circuit 130 applies a +voltage to the first output line 16a and grounds the second output line 16b. Where the signal transmitted from the coding circuit 120 is "0", the switching circuit 130 grounds the first output line 16a and applies a +voltage to the second output line 16b. Accordingly, since a signal is transmitted using the voltage polarity and not the voltage size, it may be stronger to noise.

The current limiting circuit 140 may serve to prevent a current of more than 5 mA from flowing through the human body. According to an aspect, the current limiting circuit 140 is implemented by serially connecting resistors to the two output lines 16a and 16b of the switching circuit 130 respectively. For example, where a power voltage is 3V, the current limiting circuit 140 comprises resistors of 300 ohms serially connected to the two output lines respectively. In this case, although the transmitting electrode 11a and 11b has a substantial short circuit because of very small resistance of the human body, current flowing through the human body does not exceed 5 mA. In addition, by connecting a capacitor to each resistance in parallel, it is possible to remove a high frequency component of the signal transmitted to the human body and perform electric matching with the human body, so that signal-transmitting performance may be improved.

The signal passing the current limiting circuit 140 is applied to the two transmitting electrodes 11a and 11b and is transmitted to the outside of the human body through the human body. In a conventional frequency communication method, a high frequency signal of several hundred MHz may be required, however, according to an exemplary embodiment, a video signal captured by the capsule type endoscope may be transmitted to the outside of the human body with a lower frequency signal, for example, a low frequency signal of 10 MHz.

Figure 5:
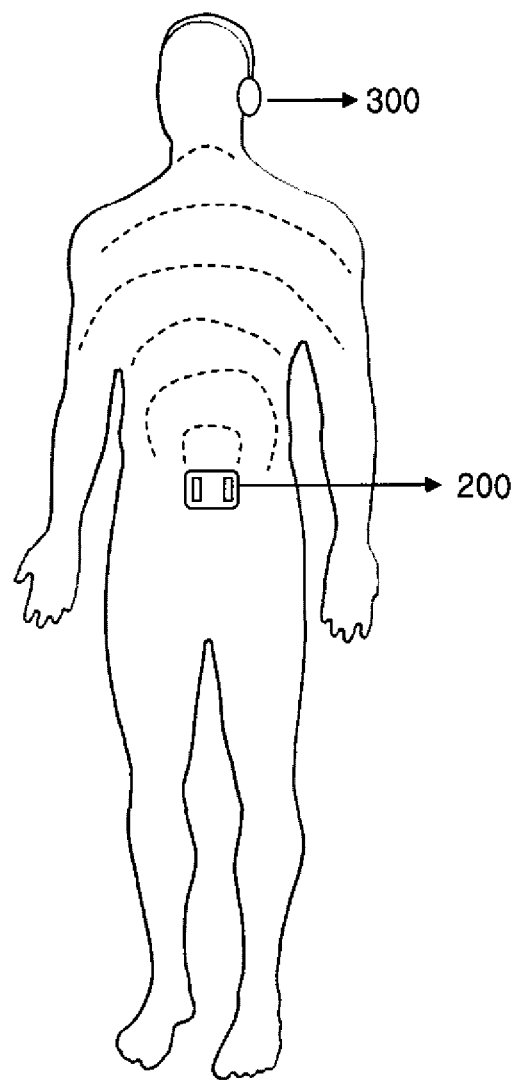
FIG. 5 is a diagram illustrating a method for data communication with respect to the human body in accordance with an exemplary embodiment.

FIG. 5 illustrates a method and system for data communication with respect to a body, for example, the human body, in accordance with an exemplary embodiment.

As shown in FIG. 5, a method for data communication with respect to a living body such as the human body may be utilized by a portable device 200 and/or a peripheral device 300. As a non-limiting illustration only, the portable device 200 may be a content player such as an MP3 Player, a cellular phone, a Portable Media Player (PMP), and/or a navigation device, etc., As a non-limiting illustration only, the peripheral device 300 may be a headset, an earset, an earphone, and/or a visual visor, etc., FIGS. 6a through 6c illustrate an exemplary portable device 200 to which a method for data communication with respect to a living body is applied in accordance with an exemplary embodiment.

As shown in FIGS. 6a-6c, the portable device 200 comprises a body 210 for housing components (not shown) such as a circuitry and/or a battery therein. For example, an upper surface or a front surface of the portable device 200 may be provided with a display unit 211, and an interfacing unit 212 for receiving an input from a user.

Two or more transmitting electrodes 253 and 254 may be formed at a rear surface of the portable device 200.

Referring to FIG. 6a, the two or more transmitting electrodes 253 and 254 may be implemented in the form of clips. Here, the clips may be formed of synthetic resins, and the transmitting electrodes 253 and 254 may be formed by plating (or coating) a conductive material on the clips.

In FIG. 6a, the two transmitting electrodes 253 and 254 are disposed on a rear surface of the portable device 200 in the form of clips. However, where the two transmitting electrodes 253 and 254 are electrically isolated from each other with a sufficient distance therebetween, the two transmitting electrodes 253 and 254 may be formed on an outer surface of the portable device 200 in any shape.

Referring to FIGS. 6b and 6c, the two transmitting electrodes 253 and 254 may be protruding from a rear surface of the portable device 200 so as to easily contact the living body. Here, the portable device 200 may include bands 261 and 262 by which the portable device 200 may be removably fixed to the living body.

As shown in FIG. 6b, each of the two transmitting electrodes 253 and 254 may be implemented as two circles and one straight line connecting the two circles. The two transmitting electrodes 253 and 254 may be spaced from each other with a distance therebetween so as to easily contact even a curved portion of the living body.

As shown in FIG. 6c, each of the transmitting electrodes 253 and 254 may be formed to have an 'L' shape so as to increase the contact area. Here, the transmitting electrodes 253 and 254 may be formed in different directions so as to maintain a sufficient distance therebetween.

Figure 7:
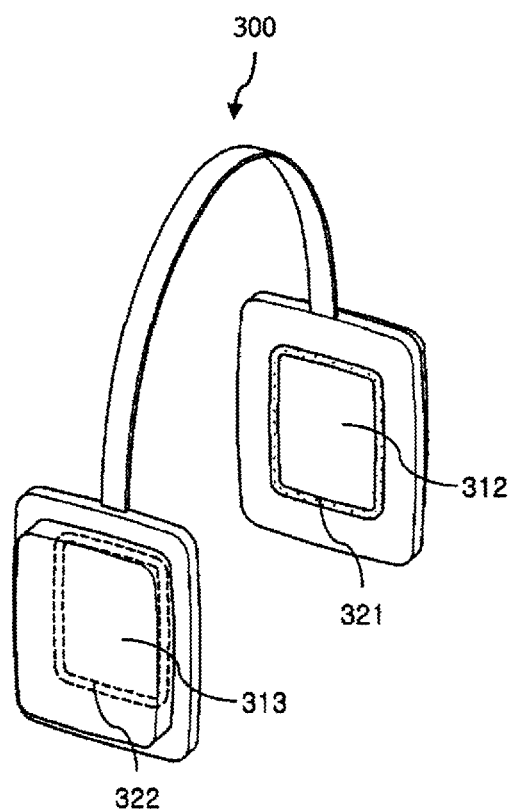
FIG. 7 is a perspective view of a peripheral device to which a method for data communication with respect to the human body is applied in accordance with an exemplary embodiment.

FIG. 7 illustrates an exemplary peripheral device 300 to which a method for data communication with respect to a living body is applied in accordance with an exemplary embodiment.

As shown in FIG. 7, the peripheral device 300, e.g., the headset 300 comprises one or more speakers 312 and 313, and two receiving electrodes 321 and 322 provided to contact the living body. The receiving electrodes 321 and 322 may be a conductive material.

Figure 6:
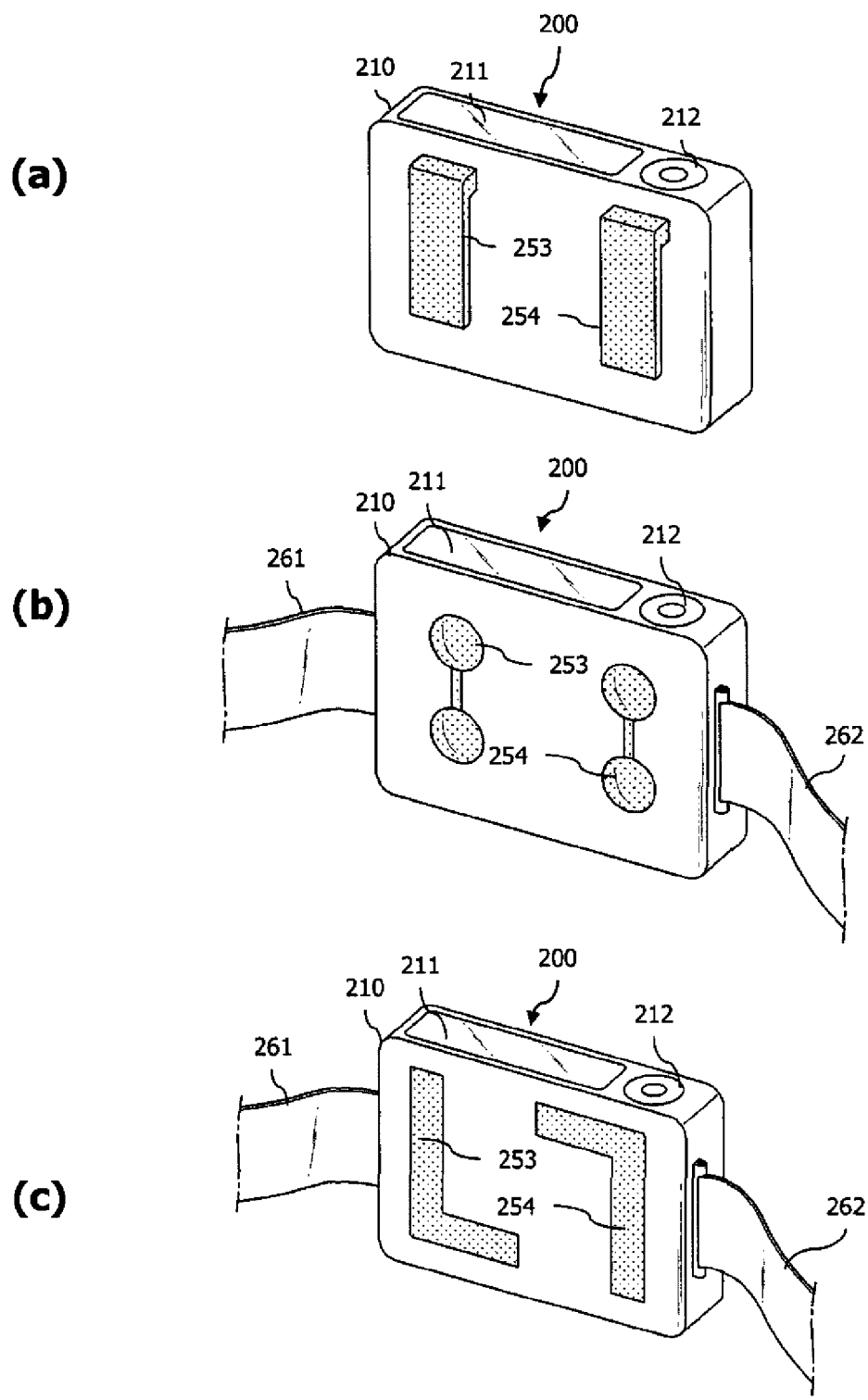
FIGS. 6a through 6c are perspective views illustrating a portable device to which a method for data communication with respect to the human body is applied, in accordance with exemplary embodiments.
Figure 8:
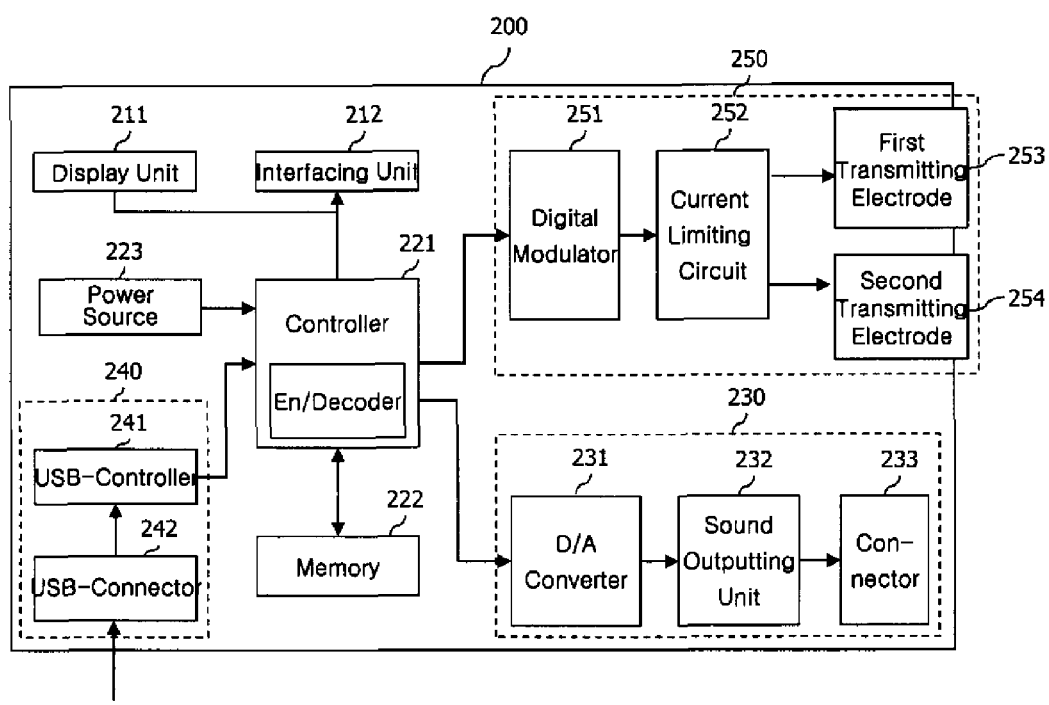
FIG. 8 is a block diagram illustrating an internal construction of the portable device of FIG. 6 according to an exemplary embodiment.

FIG. 8 illustrates an internal construction of the portable device 200 of FIG. 6 according to an exemplary embodiment.

As shown in FIG. 8, the portable device 200 comprises a display unit 211 for displaying a content, an interfacing unit (or button unit) 212 for receiving a user's manipulation, a controller 221, a memory (or a data storage) 222, a power source 223, a sound output unit 230, a data input/output unit 240, and a transmitting unit 250.

The controller 221 comprises an encoder/decoder for decoding a sound source and/or image signals of a content stored in the memory 222 to thereby output the content, or encoding a sound source and/or image signals of an inputted content to thereby store the content in the memory 222.

The sound output unit 230 comprises a D/A converter 231 for converting digital signals into analogue signals, for example, the digital signals corresponding to the sound source of the content being decoded, a sound outputting unit 232 for outputting the converted analogue signals as sound, and a connector 233 for providing a connection to, for example, an earphone and/or a headset.

The data input/output unit 240 comprises a Universal Serial Bus (UBS) controller 241 and a USB connector 242.

The transmitting unit 250 comprises a digital modulator 252 for modulating digital signals decoded by the controller 221, a current limiting circuit 252 for limiting a current of the modulated digital signals to a predetermined value, for example, to have a value harmless or tolerable to the living body, and two transmitting electrodes 253 and 254.

The digital modulator 252 modulates the digital signals such that a plus or "1" is represented as a first state when the first transmitting electrode has a higher electric potential and the second transmitting electrode has a lower electric potential, and a negative or "0" is represented as a second state when the first transmitting electrode has a lower electric potential and the second transmitting electrode has a higher electric potential. The current limiting circuit 252 limits the current of the modulated digital signals to the predetermined value, thereby to supply a conduction current from the transmitting electrode having higher electric potential to the body, so that the conduction current in form of digital flows through the surface of the body back into the inside of the body and sinks the conduction current to the transmitting electrode having lower electric potential.

Figure 9:
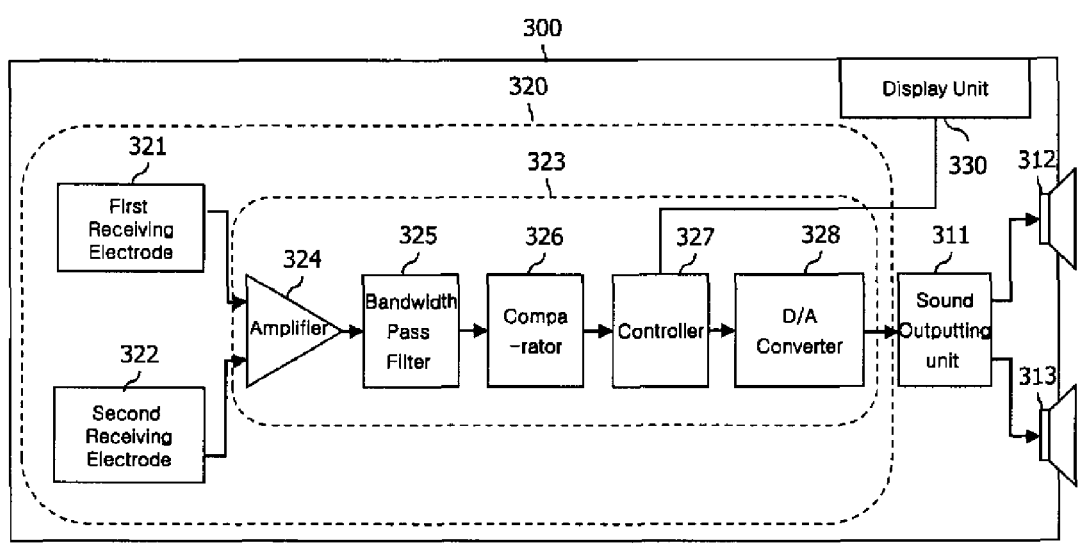
FIG. 9 is a block diagram illustrating an internal construction of the peripheral device of FIG. 7 according to an exemplary embodiment.

FIG. 9 illustrates an internal construction of the peripheral device 300 of FIG. 7 according to an exemplary embodiment.

As shown in FIG. 9, the peripheral device 300, e.g., the headset 300 comprises one or more speakers 312 and 313, a sound outputting unit 311 for applying electric signals to the speakers 312 and 313, and a receiving unit 320.

The receiving unit 320 comprises first and second receiving electrodes 321 and 322 for receiving digital electric signals corresponding to at least one of a sound source and image(s) of content, and a signal processor 323.

The signal processor 323 comprises an amplifier 324 for amplifying digital electric signals received through the first and second receiving electrodes 321 and 322, a bandwidth pass filter 325 for extracting digital baseband signals from the amplified digital electric signals, a comparator 326 for converting the digital baseband signals to signals of a predetermined voltage, a controller 327 for dividing image signals and sound source signals from each other from the digital signals, and a D/A converter 328 for converting the sound source signals of the digital signals into analogue signals.

The sound source signals converted into the analogue signals are outputted to the speakers 312 and 313 through the sound outputting unit 311.

As shown, the peripheral device 300 may further comprise a display unit 330. The controller 327 displays the images of the content by providing the image signals of the digital signals to the display unit 300.

Figure 10:
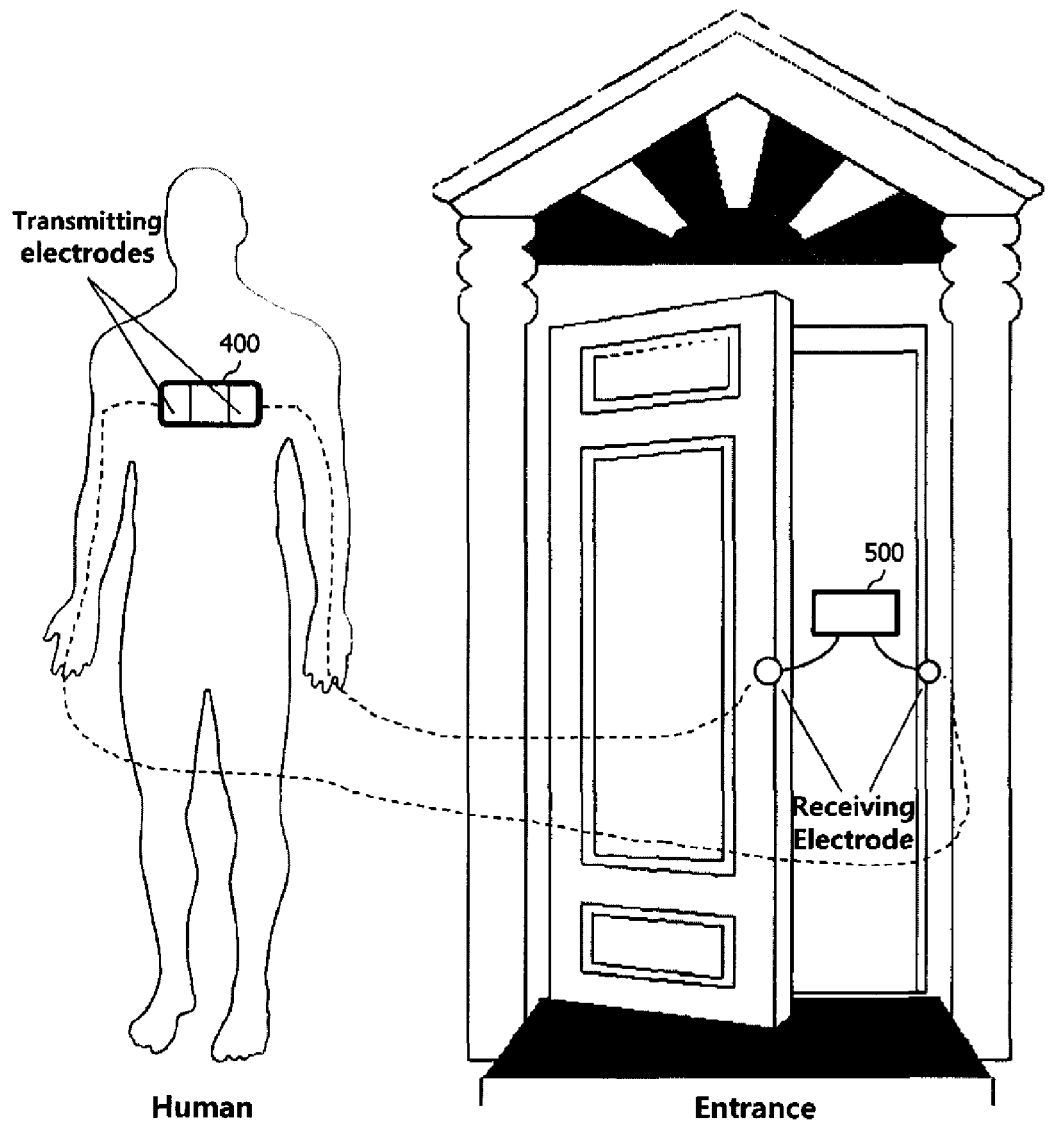
FIG. 10 is a diagram illustrating a method for data communication with respect to the human body in accordance with an exemplary embodiment.

FIG. 10 illustrates a method for data communication with respect to a living body in accordance with an exemplary embodiment.

As shown in FIG. 10, a method for data communication with respect to a living body may be applied to a security system, e.g., a door opening/closing system. As shown, a transmitting device (or an access requesting device) 400 comes in contact with the living body, for example, the human body, and a receiving device 500 is mounted to a door. One or more electronic keys may be stored in the transmitting device 400, and the transmitting device 400 includes two transmitting electrodes. The receiving device 500 includes receiving electrodes 500 that may come into contact with the living body, for example, through the hands of the user. The electronic keys of the transmitting device 400 may be transmitted to the receiving device 500 through the living body by the transmitting device 400, thereby opening and closing the security system, i.e., the door.

Figure 11:
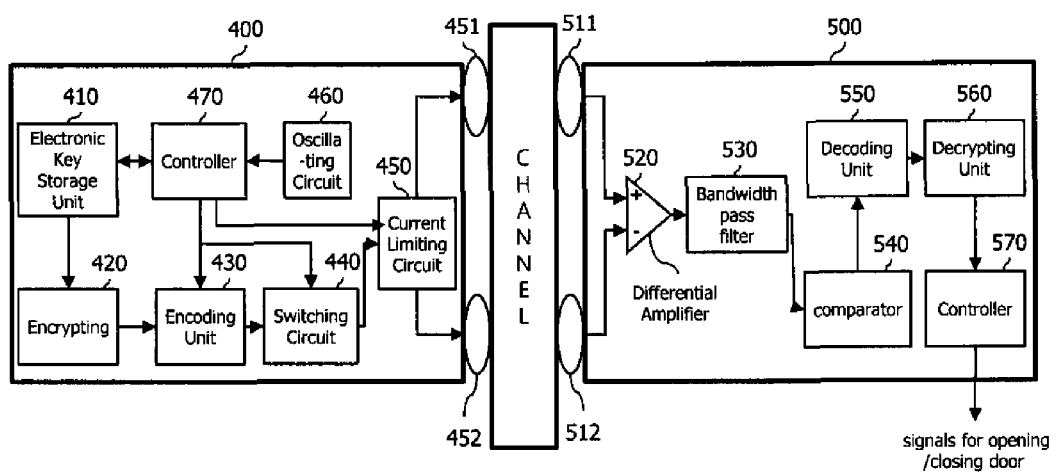
FIG. 11 is a diagram illustrating an implementation of the embodiment of FIG. 10 according to an exemplary embodiment.

FIG. 11 illustrates an implementation of the embodiment of FIG. 10 according to an exemplary embodiment.

FIG. 11 shows the transmitting device 400 and the receiving device 500.

The transmitting device 400 comprises an electronic key storage unit 410, an encrypting unit 420, an encoding unit 430, a switching circuit 440, a current limiting circuit 450, two transmitting electrodes 451 and 452, an oscillating circuit 460, and a controller 470.

Electronic keys stored in the electronic key storage unit 410 are drawn out by the controller 470, and are encrypted by the encrypting unit 420. The encrypted electronic keys are outputted as encoded signals by the encoding unit 430. The encoded signals are modulated by the switching circuit 440 so as to be outputted to the current limiting circuit 450. The current limiting circuit 450 adjusts the signals to a current having a predetermined value, for example, signals not having a current value that is harmful to the living body, and outputs the adjusted signals to the transmitting electrodes 451 and 452. The outputted current flows to the receiving device 500 through the living body.

In more detail, the switching circuit 440 modulates the encoded signals such that a plus or "1" is represented as a first state when the first transmitting electrode has a higher electric potential and the second transmitting electrode has a lower electric potential, and a negative or "0" is represented as a second state when the first transmitting electrode has a lower electric potential and the second transmitting electrode has a higher electric potential. And, the current limiting circuit 450 limits the current of the encoded signals to the predetermined value, thereby to supply a conduction current from the transmitting electrode having higher electric potential to the body, so that the conduction current in form of digital flows through the surface of the body back into the inside of the body and sinks the conduction current to the transmitting electrode having lower electric potential.

As shown, the receiving device 500 comprises two receiving electrodes 511 and 512, an amplifier 520, a bandwidth pass filter 530, a comparator 540, a decoding unit 550, a decrypting unit 560, and a controller 570.

A current is received through the two receiving electrodes 511 and 512, and the received current is amplified by the amplifier 520. Then, the received current passes through the bandwidth pass filter 530, thereby changing into baseband signals. The changed baseband signals are converted into predetermined voltages by the comparator 540, and decoded and/or decrypted by the decoding unit 550 and/or the decrypting unit 560, thereby being outputted to the controller 570. The controller 570 reads the decrypted signals, and checks whether the read signals are consistent with pre-stored electronic keys, thereby outputting control signals for controlling opening/closing of a door.

Since certain embodiments disclosed above uses a low frequency and current instead of a high frequency through antenna, when communicating with a sensor in the human body, it may reduce power consumption and attenuation in the human body, have little to no effect on external interference, and/or cause little to no damage to the human body. Since a signal is transmitted using voltage polarity, it may be strong to noise, and accordingly, receiving sensitivity may be improved.

In addition, a sensor in accordance with certain embodiments disclosed above may not need a radio transmitter and antenna, and also may not need an additional memory because it processes video signals sequentially along the passage of time. Accordingly, a small-sized and low-priced capsule type endoscope may be provided.

It is understood that while a method for data communication has been disclosed with respect to the human body, it is not limited thereto, and that the certain methods, apparatuses, and/or systems described above may be applied accordingly to a body other than the human body, for example, to an animal body.

The methods described above may be recorded, stored, or fixed in one or more computer readable media that includes program instructions to be implemented by a computer to cause a processor to execute or perform the program instructions. The media may also include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations and methods described above.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A receiver for receiving data communicated using a body as a conductor to transmit the date, the receiver comprising:
    receiving electrodes to contact the body to receive a signal corresponding to the data generated by a portable device fixed to the body; and
    a signal processor to process the signal received through the receiving electrodes, wherein the signal has a current defined to a predetermined value,
    wherein the current is generated by electric potential difference between transmitting electrodes installed on a surface of the portable device, the current flowing through a surface of the body.

2. The receiver of claim 1, wherein:
    the receiver is a peripheral device to output a reproduction signal corresponding to video and/or audio data,
    the processed signal corresponds to an output obtained from reproducing the video and/or audio data, and
    the peripheral device further comprises an output unit to output the signal from the signal processor.

3. The receiver of claim 2, wherein the peripheral device is one of a headset, an earset, an earphone, a visual visor, and a combination thereof.

4. The receiver of claim 2, wherein the output unit comprises at least one of:
    a sound outputting unit to output sound corresponding to the signal; and
    a display unit to output an image corresponding to the signal.

5. The receiver of claim 4, wherein the signal processor comprises:
    an amplifier to amplify the signal received through the receiving electrodes;
    a bandwidth pass filter to extract a baseband signal from the amplified signal;
    a comparator to convert the baseband signal to a signal of a predetermined voltage; and
    a controller unit to divide the converted signal and output the divided signals to the output unit.

6. The receiver of claim 1, wherein:
    the data corresponds to an electronic key, and
    the receiver further comprises a controller to control access based on the signal received through the receiving electrodes.

7. The receiver of claim 6, wherein the signal processor comprises:
    an amplifier to amplify the signal received through the receiving electrodes;
    a bandwidth pass filter to convert the amplified signal to a baseband signal;
    a comparator to convert the baseband signal to a signal of a predetermined voltage;
    a decoding unit to decode the signal of a predetermined voltage; and
    a decrypting unit to decrypt the decoded signal to output to the controller.

* * * * *